(12) United States Patent
Oshima et al.

(10) Patent No.: US 6,700,947 B2
(45) Date of Patent: Mar. 2, 2004

(54) APPARATUS FOR OPTICALLY TRANSMITTING DATA BETWEEN ROTOR AND STATOR AND X-RAY CT APPARATUS HAVING THE APPARATUS INCORPORATED THEREIN

(75) Inventors: Shigeru Oshima, Yokohama (JP); Hiroshi Matsuyama, Kawasaki (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 221 days.

(21) Appl. No.: 09/905,874

(22) Filed: Jul. 17, 2001

(65) Prior Publication Data

US 2002/0015469 A1 Feb. 7, 2002

(30) Foreign Application Priority Data

Jul. 18, 2000 (JP) ........................................ 2000-217531

(51) Int. Cl.$^7$ ................................................. H05G 1/60
(52) U.S. Cl. .......................................... 378/15; 378/19
(58) Field of Search ............................ 378/15, 19, 23

(56) References Cited

U.S. PATENT DOCUMENTS

| 4,519,670 A | * | 5/1985 | Spinner et al. ............... 385/25 |
| 4,555,631 A | * | 11/1985 | Martens ....................... 250/551 |
| 4,796,183 A | * | 1/1989 | Ermert et al. ................. 378/10 |
| 4,943,137 A | * | 7/1990 | Speer ........................... 385/26 |
| 5,134,639 A | * | 7/1992 | Vekstein et al. .............. 378/15 |
| 5,229,871 A | * | 7/1993 | Czarnek et al. ............... 359/15 |
| 5,469,488 A | | 11/1995 | Ono |
| 6,385,367 B1 | * | 5/2002 | Rogers et al. ................ 385/26 |

* cited by examiner

*Primary Examiner*—Louis Arana
(74) *Attorney, Agent, or Firm*—Oblon, Spivak, McClelland, Maier & Neustadt, P.C.

(57) ABSTRACT

Disclosed is a light transmitting apparatus between a rotor and a stator for transmitting data. The apparatus comprises a light-emitting element arranged in a position of a first reference radius of the rotor for emitting a light beam in accordance with the data to be transmitted, a photo-detecting element arranged in a position of a second reference radius on the stator 12 for detecting the beam, and a fan-shaped optical guide member positioned between the stator and the rotor, made of a transparent material, and fixed to the stator. The beam is reflected by a first reflecting surface formed in the arcuate portion of the member and, then, reflected by a second reflecting surface formed in the proximal end portion of the member so as to guide the beam to the photo-detecting element.

20 Claims, 7 Drawing Sheets

APPARATUS FOR OPTICALLY TRANSMITTING DATA BETWEEN ROTOR AND STATOR AND X-RAY CT APPARATUS HAVING THE APPARATUS INCORPORATED THEREIN

CROSS-REFERENCE TO RELATED APPLICATIONS

This application is based upon and claims the benefit of priority from the prior Japanese Patent Application No. 2000-217531, filed Jul. 18, 2000, the entire contents of which are incorporated herein by reference.

BACKGROUND OF THE INVENTION

1. Field of the Invention

The present invention relates to an apparatus for optically transmitting data between a rotor and a stator and an X-ray CT apparatus having the apparatus incorporated therein.

2. Description of the Related Art

Known is an optical transmission apparatus for transmitting data by utilizing an optical beam transmitted in the space between a rotor and a stator. In the optical transmission apparatus, a cable is not used and, thus, the rotation of the rotor is not restricted so that the rotor can be freely rotated. In addition, a mechanical contact or contacts are not required in the optical transmission apparatus unlike the transmission apparatus using a slip ring, leading to a high reliability.

The particular optical transmission apparatus is used, for example, in an X-ray CT (computed-tomography) apparatus, which is one of medical image diagnostic apparatuses. The X-ray CT apparatus comprises a hollow rotor and a hollow stator, and a patient (human body) is put in the bore of the X-ray CT apparatus. An X-ray tube and an X-ray detector are arranged in the rotor, and the patient put in the X-ray CT apparatus is irradiated with an X-ray emitted from the X-ray tube while rotating the rotor to permit the X-ray to scan, for example, spirally the patient. The X-ray passing through the patient is detected by the X-ray detector so as to be taken out as an electric signal. This electric signal is converted into a digital signal and, then, converted again into a light beam so as to be transmitted to the side of the stator. The light beam transmitted to the side of the stator is received by a photo-detecting element and is converted into an electric signal, and the electric signal is processed to obtain a tomographic image information or data of the patient.

In the optical transmission apparatus between the rotor and the stator utilized in the conventional X-ray CT apparatus, a plurality of light-emitting elements 83, e.g., 64 light-emitting elements 82, are arranged at a predetermined interval on a circle having a predetermined radius on a rotor 81, as shown in FIG. 1. For simplifying the drawing, only two light-emitting elements 83a and 83b are shown in FIG. 1. Also, a single photo-detecting element 84 is arranged on a circle having the radius equal to that noted above on a stator 82. A light beam modulated in accordance with the image data is transmitted between the light-emitting element 83 and the photo-detecting element 84. In accordance with rotation of the rotor 81, the light-emitting elements 83a and 83b are successively faced to the photo-detecting element 84. FIG. 1 shows the state immediately after the light-emitting element 83a has being faced to the photo-detecting element 84 and the state immediately before the light-emitting element 83b reaches the photo-detecting element 84.

Light beams 85a, 85b emitted from the light-emitting elements 83a, 83b is diverged, respectively. In the state shown in FIG. 1, the photo-detecting element 84 is positioned intermediate between the light-emitting elements 83a and 83b so as to receive the edge portions of the light beams 85a, 85b, i.e., the weak portions of the light power. However, since the photo-detecting element 84 simultaneously receives the two light beams 85a, 85b, the power of the received light beams (incident light intensity) is maintained at a relatively high level.

In order to ensure a sufficiently high optical power even in the case where the photo-detecting element 84 is positioned intermediate between the light-emitting elements 83a and 83b, it is necessary to set the distance between the light-emitting elements 83a and 83b such that the light beams 85a, 85b emitted the light-emitting elements 83a, 83b are allowed to partially overlap each other, as shown in FIG. 1. Because of this requirement, the number of light-emitting elements is increased. For example, it is necessary to arrange 64 light-emitting elements. In this connection, the number of IC's for driving the light-emitting elements and the wiring for connecting these IC's is increased, leading to serious problems. For example, the power consumption is increased. In addition, the reliability is lowered and the manufacturing cost is increased.

In order to avoid the problems pointed out above, it may be advisable to increase the distance between the rotor 81 and the stator 82 so as to widen the distribution of the light beams emitted from the light-emitting elements and, thus, to decrease the number of photo-detecting elements. It should be noted in this connection, however, that the intensity of light is inversely proportional to the square of the distance. In other words, if the distance between the rotor 81 and the stator 82 is increased, the power of light received by the photo-detecting element is weakened so as to give rise to a new problem that a transmission error is increased.

The X-ray CT apparatus is required in recent years to transmit a large amount of data at a high speed by the shortening of the irradiating time and the employment of a multi-slice system for acquiring a large number of tomographic images simultaneously. In this connection, transmission of a large amount of data at a high speed is required in respect of the optical transmission apparatus between the rotor and the stator. However, it is difficult for the conventional construction described above to satisfy the particular requirement because of the reasons described below.

Concerning the specific parts used in the optical transmission apparatus between the rotor and the stator, it is possible to use a light-emitting diode (LED) or a laser diode (LD) as the light-emitting element. In the case of transmitting the data of a large capacity roughly exceeding hundred Mbps at a high transmitting speed, an LD is used in many cases. On the other hand, a photodiode (PD) is generally used as the photo-detecting element. The LD and the PD have characteristic parameters called the maximum light output and the minimum light receiving sensitivity, respectively. An allowable loss called optical power budget is determined by the values of these characteristics parameters.

In order to achieve an error-free data transmission by the light beam between the rotor and the stator, it is necessary to make the optical power budget as large as possible. On the other hand, in view of the increase in the data transmission, the light output of the LD tends to be decreased with increase in the data transmission speed. Also, in order to increase the data transmission speed for the PD, it is necessary to decrease the parasitic capacitance so as to diminish the light receiving area, with the result that the received optical power is decreased. It follows that the optical power budget is diminished with increase in the data transmission speed.

It should be noted that, if the transmission speed is increased with the distance between the adjacent light-emitting elements set constant, the light receiving power of the photo-detecting element is diminished in accordance with the transmission speed. Therefore, it is necessary to arrange the light-emitting elements at a higher density in order to ensure a desired light receiving power so as to make the above-noted problems more serious in respect of the increase in the power consumption accompanying the increase in the number of light-emitting elements used as well as the reduction in the reliability and the increase in the manufacturing cost.

As described above, in the conventional light transmission apparatus between a rotor and a stator for performing the data transmission directly by the light beam from a plurality of light-emitting elements arranged in the circumferential direction on the side of the stator toward the photo-detecting element arranged on the side of the stator, it is necessary to arrange a large number of light-emitting elements on the side of the rotor, leading to the problems such as the increase in the power consumption, the reduction of the reliability and the increase in the manufacturing cost. Also, where it is intended to achieve the transmission of a large capacity of data at a high speed as required for an X-ray CT apparatus, the light receiving area of the photo-detecting element is diminished so as to decrease the optical power budget. Therefore, it is necessary to arrange the light-emitting elements at a higher density so as to make the above-noted problems more serious.

BRIEF SUMMARY OF THE INVENTION

An object of the present invention is to provide a light transmitting apparatus between a rotor and a stator capable of effectively decreasing the number of light-emitting elements so as to lower the power consumption, to improve the reliability and to achieve the cost reduction, thereby making the apparatus adapted for the large capacity data transmission at a high speed.

Another object of the present invention is to provide an X-ray CT apparatus provided with the particular light transmitting apparatus between the rotor and the stator.

According to one aspect of the present invention, there is provided an apparatus for transmitting a light beam modulated in accordance with data to be transmitted between a rotor and a stator, the rotor and stator facing each other, and coaxial first and second reference circles having first and second different radii being defined on the rotor and stator respectively, the apparatus comprising:

a light-emitting element configured to emit a light beam in accordance with the data to be transmitted, the light-emitting element being mounted on the rotor and arranged on the first reference circle;

a photo-detecting element configured to detect the light beam emitted from the light-emitting element, the photo-detecting element being mounted on the stator and arranged on the second reference circle; and an optical guide member configured to guide the light beam emitted from the light-emitting element to the photo-detecting element, the optical guide member being arranged between the stator and the rotor, made of a transparent material, and fixed to one of the stator and the rotor.

According to another aspect of the present invention, there is provided an apparatus for transmitting a light beam modulated in accordance with data to be transmitted between a rotor and a stator, the rotor and stator facing each other, and coaxial first and second reference circles having first and second different radii being defined on the rotor and stator respectively, the apparatus comprising:

groups of light-emitting elements, each group configured to emit a light beam in accordance with the same data to be transmitted, the light-emitting elements being mounted on the rotor and arranged at predetermined intervals on the first reference circle;

photo-detecting elements corresponding to the groups of the light-emitting elements and each configured to detect the light beams emitted from each of the groups of the light-emitting elements, the photo-detecting elements being equidistantly mounted on the stator and arranged on the second reference circle, and the groups of the photo-detecting elements being equal in number to the groups of the light-emitting elements; and optical guide members each configured to guide the light beam emitted from the group of the light-emitting element to the corresponding photo-detecting element, the optical guide members being arranged between the stator and the rotor, made of a transparent material, and fixed to one of the stator and the rotor.

According to further aspect of the present invention, there is provided an X-ray CT apparatus comprising:

a X-ray tube configured to emit X-rays;

a rotor configured to support the X-ray tube, on which a first reference circle having a first radius is defined;

a stator configured to rotatably support the rotor, on which a second the rotor reference circle having a second radius is defined, the first and second circles being coaxially arranged and the stator facing to the rotor;

a driving mechanism configure to rotate the rotor with the X-ray tube;

a light-emitting element configured to emit a light beam in accordance with the data to be transmitted, the light-emitting element being mounted on the rotor and arranged on the first reference circle;

a photo-detecting element configured to detect the light beam emitted from the light-emitting element, the photo-detecting element being mounted on the stator and arranged on the second reference circle; and an optical guide member configured to guide the light beam emitted from the light-emitting element to the photo-detecting element, the optical guide member being arranged between the stator and the rotor, made of a transparent material, and fixed to one of the stator and the rotor.

To be more specific, the optical guide member is formed of, for example, a fan-shaped transparent plate having an arcuate portion and a proximal end portion, and includes a tapered first reflecting surface formed in the arcuate portion at a predetermined angle relative to the optical axis of the light-emitting element, and a second reflecting surface formed in the proximal end portion substantially in parallel to the first reflecting surface.

According to one embodiment of the present invention, the optical guide member formed of a fan-shaped transparent plate is fixed to the stator to permit the arcuate portion to be located in a position of a first reference radius and to permit the proximal end portion to be located in a position of a second reference radius such that the light beam emitted from the light-emitting element is successively reflected in the first reflecting surface and, then, in the second reflecting surface so as to guide the light beam to the photo-detecting element.

According to another embodiment of the present invention, the optical guide member formed of a fan-shaped transparent plate is fixed to the rotor to permit the arcuate portion to be located in a position of the second reference radius and to permit the proximal end portion to be located in a position of the first reference radius such that the light beam emitted from the light-emitting element is successively reflected in the second reflecting surface and, then, in the first reflecting surface so as to guide the light beam to the photo-detecting element.

As described, in the present invention, a major portion of the light beam emitted from the light-emitting element is transmitted to reach the photo-detecting element through the optical guide member, making it possible to ensure a sufficient received light power in the photo-detecting element without arranging a large number of light-emitting elements at a small interval. Also, since the reduction of the received light power is small even where the light-emitting elements and the photo-detecting element are arranged apart from each other, it is possible to achieve a low power consumption, to improve the reliability and to achieve the cost saving by decreasing the number of light-emitting elements. Further, even if the light receiving area of the photo-detecting element is diminished in an attempt to increase the operating speed, it is possible to ensure a sufficient received light power so as to make it possible to achieve the data transmission by utilizing the light beam low in transmission error.

DETAILED DESCRIPTION OF THE INVENTION

Some embodiments of the present invention will now be described with reference to the accompanying drawings in respect of an apparatus for optically transmitting data between a rotor and a stator and an X-ray CT apparatus having the particular optical data transmitting apparatus incorporated therein.

Figure 1:
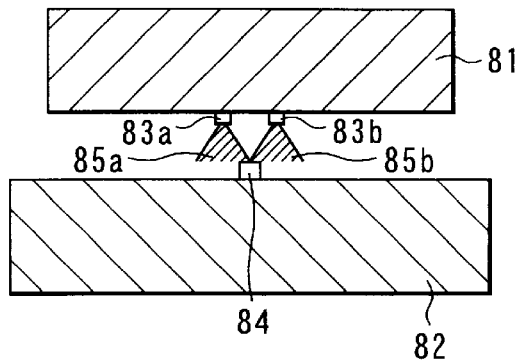
FIG. 1 schematically shows the basic principle of the conventional light transmitting apparatus between a rotor and a stator.
Figure 2:
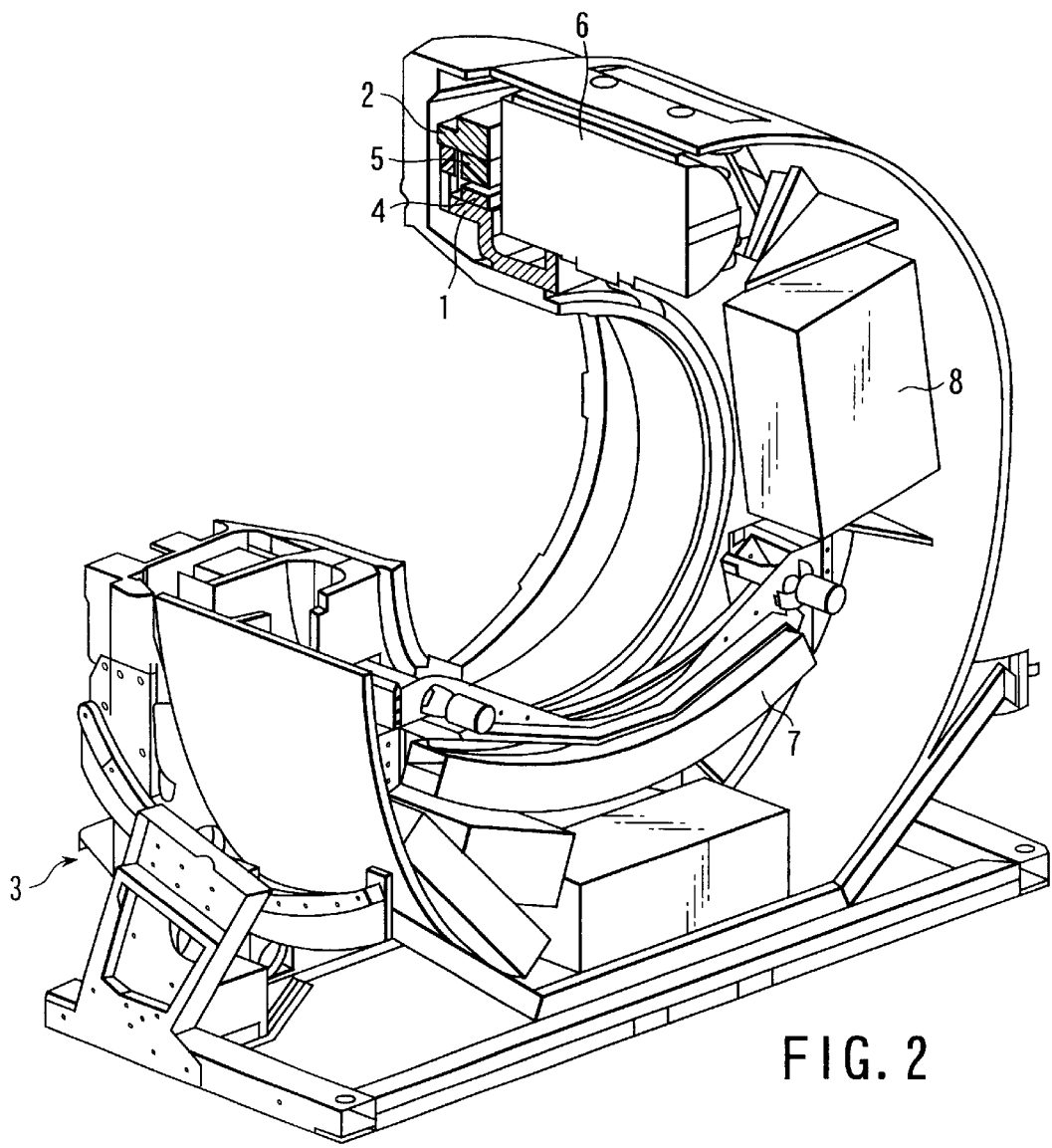
FIG. 2 is an oblique view, partly broken away, schematically showing the construction of an X-ray CT apparatus to which is applied the light transmitting apparatus according to an embodiment of the present invention.

Let us describe first an X-ray CT apparatus incorporated with an apparatus for optical data transmission between a rotor and a stator cording to the present invention. FIG. 2 is an oblique view, with a gantry partly broken away, showing an X-ray CT apparatus of the present invention. An annular rotor 1 is rotatably supported by an annular stator 2 arranged substantially perpendicular to a stand 3. Rotor yokes 4 each consisting of a permanent magnet and an annular magnetic body are equidistantly mounted to the circumferential surface of the rotor 1. The rotor yoke 4 and a coil 5 mounted to the stator 2 collectively constitute a direct drive motor system for directly transmitting the motor driving force to the rotor 1 so as to rotate the rotor 1.

An X-ray tube 6 for emitting an X-ray in the shape of, for example, a fan-shaped beam and an X-ray detection array 7 of a multi-slice shape are mounted to the rotor 1 in a manner to have a patient or to-be-examined body on a bed (not shown) located therebetween. Also mounted to the rotor 1 is a data acquisition system (DAS) 8 comprising, for example, a current-voltage converter for converting the current signal into a voltage signal, an integrator for periodically integrating the voltage signal, a preamplifier for amplifying the output signal of the integrator, and an A/D converter for converting the output signal of the preamplifier into digital data.

Figure 3B:
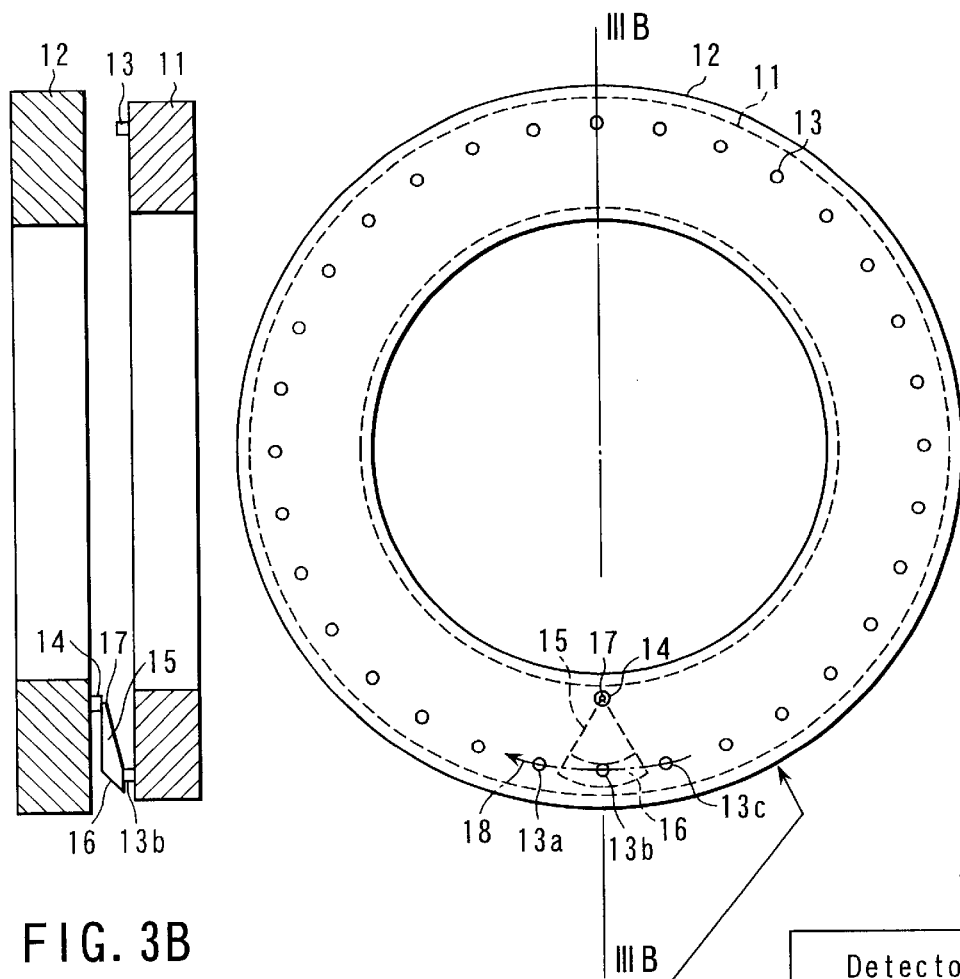
FIG. 3B is a cross sectional view along the line IIIA–IIIA' shown in FIG. 3A.
Figure 3A:
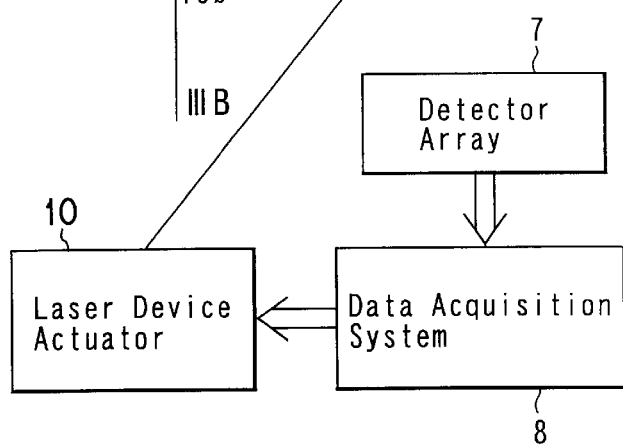
FIG. 3A is a front view schematically showing an apparatus for a light transmission between a rotor and a stator according to a first embodiment of the present invention.

The digital data generated from the data acquisition system 8 is supplied to a laser device actuator 10 shown in FIG. 3A, which is mounted to the rotor 1, and a driving signal is supplied from the laser device actuator 10 to the light-emitting element in accordance with the digital data. Further, data is transmitted in the form of a light beam from the light-emitting element to the photo-detecting element mounted to the stator 2. To be more specific, a light beam modulated in accordance with the digital data is generated from the light-emitting element so as to be transmitted to the photo-detecting element.

Let us describe some embodiments of the present invention in respect of the apparatus for the light transmission between a rotor and a stator in which the digital data generated from the data acquisition system 8 is transmitted in the form of a light beam in the X-ray CT apparatus of the construction described above.

First Embodiment

FIGS. 3A and 3B collectively show an apparatus for the light transmission between a rotor and a stator according to the first embodiment of the present invention. A rotor 11 and a stator 12 shown in FIGS. 3A and 3B correspond respectively to the rotor 1 and the stator 2 shown in FIGS. 2A and 2B. Each of these rotor 11 and stator 12 is annular, and these rotor 11 and stator 12 are arranged on the same axis apart from each other in a manner to face each other.

A plurality of light-emitting elements 13, i.e., 32 light-emitting elements 13 in this embodiment, are equidistantly arranged on circular positions defined by a first reference radius on that surface of the rotor 11 which is positioned to face the stator 12. In this embodiment, the light-emitting elements 13 are arranged on circular positions close to the outer circumferential surface of the rotor 11. On the other hand, a single photo-detecting element 14 is arranged on a circular position defined by a second reference radius on that surface of the stator 12 which faces the rotor 11. The circular positions defined by the first and second reference radii have a same a center and have a coaxial arrangement. However, the circular positions defined by the first reference radius referred to previously differ from the circular position defined by the second reference radius noted above. In this embodiment, the photo-detecting element 14 is arranged on a circular position close to the inner circumferential surface of the stator 12. It is possible for the light-emitting element 13 to be formed of a light-emitting diode (LED). In this embodiment, however, a laser diode (LD) capable of achieving a high speed operation compared with an LED is preferably used for forming the light-emitting element 13. It is basically possible for the photo-detecting element 14 to be formed of any element as far as the element is capable of converting light into an electric signal, though, for example, a photodiode (PD) is suitably used as the photo-detecting element 14.

Figure 4:
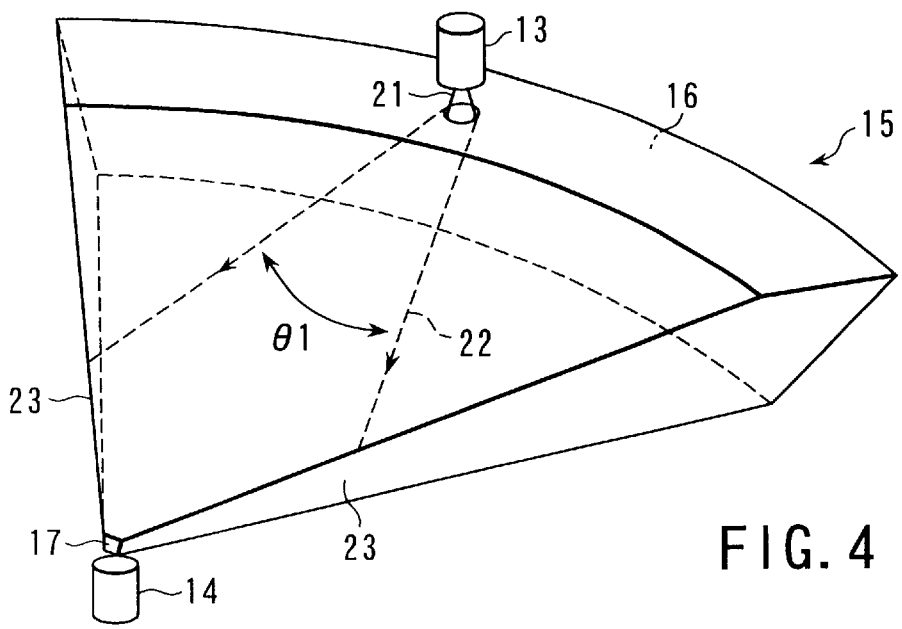
FIG. 4 is an oblique view schematically showing the construction of an optical guide member shown in FIGS. 3A and 3B.

Further, an optical guide member 15 for guiding the light beam emitted from the light-emitting element 13 into the photo-detecting element 14, the optical guide member 15 being formed of a transparent material, is fixed to that surface of the stator 12 which faces the rotor 11. The optical guide member 15 is formed of a fan-shaped transparent plate as shown in FIG. 3A and is constructed as shown in FIG. 4.

To be more specific, the optical guide member 15 is supported by a support member (not shown) on the stator 12 with a suitable spacer interposed therebetween such that the arcuate surface portion of the optical guide member 15 is located in a position on a circle defined by the first reference radius, i.e., a position through which passes the light-emitting element 13 on the rotor 11, and that the proximal end portion of the optical guide member 15 is located on a position on a circle defined by the second reference radius, i.e., the arranging position of the photo-detecting element 14 on the stator 12. The position of the proximal end portion is substantially equal to the center (curvature central portion) of the arc of the arcuate portion. A tapered first reflecting surface 16, which is inclined by a predetermined angle, e.g., 45°, relative to the optical axis of the light-emitting element 13, is formed on the outer circumferential surface of the arcuate portion of the optical guide member 15. Also, a second reflecting plane 17, which is substantially parallel to the first reflecting plane 16, is formed in the proximal end portion of the optical guide member 15. The optical guide member 15 is shaped, for example, such that the radius of the arcuate portion (radius of the fan-shaped portion) is about 10 cm, the central angle of the fan-shaped portion is 50°, and the thickness of the optical guide member 15 is 10 mm in the thickest portion and 1 mm in the thinnest portion. The dimension of the optical guide member 15 given above is no more than an example. It is possible for the radius to be about 15 cm, which is about 50% larger than that given above, or to be selected to fall within a range of between 10 cm and 15 cm. It is also possible for the central angle of the fan-shaped optical guide member 15 to fall within a range of between 35° and 50°.

By arranging the optical guide member 15 of the particular construction described above, it is possible to permit the light beam emitted from the light-emitting element 15 to be reflected successively from the first reflecting plane 16 and then from the second reflecting plate 17 so as to guide the reflected light beam to the photo-detecting element 14. FIG. 4 shows that the second reflecting plane is flat. However, the shape of the second reflecting plane 17 is not particularly limited, e.g., the second reflecting plane 17 may be curved, as far as the incident light beam can be effectively reflected so as to be guided to the photo-detecting element 14.

Let us describe the operation and the produced effect of the apparatus for the light transmission between the rotor and the stator according to the first embodiment of the present invention, with an X-ray CT apparatus taken as an example.

As shown in FIG. 3A, the signal generated from the X-ray detecting array 7 is supplied to the data acquisition system 8 so as to be converted into digital data and stored in the data acquisition system 8. The digital data collected in the data acquisition system 8 is imparted to the laser device actuator 10 mounted to the rotor 1. A driving signal is supplied from the laser device actuator 10 into the light-emitting element in accordance with the digital data, and the light beam generated from the light-emitting element is transmitted to the photo-detecting element mounted to the stator 2. In other words, a light beam modulated in accordance with the digital data is generated from the light-emitting element so as to be transmitted to the photo-detecting element.

If the rotor 11 is rotated in the clockwise direction in FIG. 3A, the light-emitting element 13 fixed to the rotor 11 is moved along the arcuate portion of the optical guide member 15 in a direction denoted by an arrow 18 so as to pass through the optical guide member 15. In FIG. 3A, the light-emitting elements 13 are positioned as follows. Specifically, immediately after the light-emitting element 13a has passed through the arcuate portion of the optical guide member 15, the light-emitting element 13b is passing over the arcuate portion of the optical guide member 15, and the light-emitting element 13c is immediately before reaching the arcuate portion of the optical guide member 15. Under this state, a light beam 21 emitted from the light-emitting element 13b, which is denoted by a reference numeral 13 in FIG. 4, is incident on the optical guide member 15 in a direction substantially perpendicular to the optical guide member 15 from a plane parallel to the rotor 11 and, then, is reflected from the first reflecting surface 16.

Further, the light beam 21 reflected from the first reflecting surface 16 passes within the optical guide member 15 and is partly reflected repeatedly by the upper and lower surfaces and a side surface 23 of the optical guide member 15 so as to arrive at the second reflecting surface 17. The light beam arriving at the second reflecting surface 17 is further reflected by the second reflecting surface 17 so as to be emitted to the outside of the optical guide member 15 and, thus, to be incident on the photo-detecting element 14.

In general, the light beam emitted from an LD used as the light-emitting element 13 is diverged. The LD used as the light-emitting element 13 in the first embodiment is of a vertical resonance type. The light beam emitted from the LD has a divergent angle of 10° in the horizontal direction and a divergent angle of 35° in the vertical direction so as to form an elliptical beam shape. The divergent angle is an angle at the half-width value of the light output.

If the light beam emitted from the light-emitting element 13 has a large divergent angle, the power of the light received by the photo-detecting element 14 is lowered. Therefore, the direction of the light-emitting element 13 is adjusted to permit the divergent angle θ1 within the plane of the optical guide member 15 to have a horizontal divergent angle (10°). It should be noted that the light beam emitted from the light-emitting element 13 is repeatedly reflected in the vertical direction by the upper and lower surfaces of the optical guide member 15 so as to arrive at the second reflecting surface 17. It follows that a particular problem is not generated even if the divergent angle in the vertical direction is large.

The light beam arriving at the photo-detecting element 14 is converted into an electric signal (photocurrent). The output signal of the photo-detecting element is subjected to, for example, the current-voltage conversion and to amplification by a preamplifier (not shown) and, then, supplied to an image processing circuit so as to reconstruct the tomographic image information of the patient.

In the conventional light transmission apparatus between a rotor and a stator in which the light beam emitted from the light-emitting element is directly incident on the photo-detecting element via a space, the light beam emitted from the light-emitting element is radially diverged. Therefore, in order to ensure a sufficient light power received by the photo-detecting element, it is necessary to allow the light beams emitted from a plurality of light-emitting elements to be incident simultaneously on the photo-detecting element by increasing the number of light-emitting elements and by decreasing the arranging interval of the light-emitting elements. As a result, various problems are generated in respect of the power consumption, the reliability and the cost. On the other hand, if the distance between the light-emitting element and the photo-detecting element is increased in an attempt to avoid the problems noted above, additional problems are generated that the light power received by the photo-detecting element is weakened, and that the transmission error is increased.

On the other hand, in the first embodiment of the present invention, the light beam 21 emitted from the light-emitting element 13 is reflected from the first reflecting surface 16 formed in the arcuate portion of the fan-shaped optical guide member 15. A relatively large light power in the central portion of a light beam 22 reflected from the first reflecting surface 16 is transmitted toward the second reflecting surface 17 formed in the proximal end portion of the optical guide member 15. Further, the light beam reflected from the second reflecting surface 17 is transmitted to arrive at the photo-detecting element 14.

To be more specific, in the first embodiment of the present invention, the most portion of the light beam emitted from the light-emitting element 13 is transmitted to arrive at the photo-detecting element 14 via the optical guide member 15, making it possible to ensure a sufficient light power received by the photo-detecting element 14 without arranging the light-emitting elements 13 at a high density as in the prior art. Also, the attenuation of the light power received by the photo-detecting element 14 is very small even if the distance between the light-emitting element 13 and the photo-detecting element 14 is large.

It follows that, in the light transmitting apparatus between the rotor and the stator according to the first embodiment of the present invention, it is possible to decrease the number of light-emitting elements 13 used so as to permit lowering the power consumption, permit improving the reliability, and permit reducing the cost. What should also be noted is that, even if the light receiving area of the photo-detecting element 14 is diminished in an attempt to achieve the high speed operation, it is possible to increase the received light power, compared with the conventional apparatus, making it possible to achieve the data transmission low in the transmission error by utilizing the light beam.

It should also be noted that the fan-shaped optical guide member 15 permits the optical path reaching the photo-detecting element 14 to be substantially constant regardless of the position on which the light beam emitted from the light-emitting element 13 is incident. As a result, deviation of the bit phase is unlikely to take place. It follows that it is possible to achieve a high speed operation easily by making uniform the wirings between the driving IC for driving the light-emitting element 13 and the light-emitting elements 13.

According to the first embodiment of the present invention, the optical guide member 15 is newly required, compared with the conventional apparatus. It is possible to use a transparent acrylic resin for forming the optical beam guide member 15. In the case of using an acrylic resin plate, the acrylic resin plate is subjected to a cutting treatment, followed by polishing the entire surface of the cut plate with abrasive grains of diamond so as to achieve a mirror-like finish. Where the surface of the polished acrylic resin plate is irregular, an irregular reflection takes place in the irregular portion so as to cause a light loss. It follows that it is particularly desirable for the reflecting surfaces 16 and 17 to be finished into a mirror-like surface.

If the optical guide member 15 is individually manufactured, the manufacturing cost is increased. However, the increase in the manufacturing cost is markedly low, compared with the cost required for the conventional light-emitting elements and the increase in the manufacturing cost of the driving IC for the light-emitting elements. Where the optical guide member 15 is manufactured on the mass production basis, the optical guide member 15 relatively low in the surface irregularity can be obtained with a relatively low cost in the case of employing a molding process using a mold. When it comes to the assembling process, the optical guide member 15 is fixed by using, for example, four spacers. In this case, it was possible to eliminate the light loss substantially completely by diminishing the contact area with the spacers. It follows that the assembling process was easier than in the case of mounting a large number of light-emitting elements as in the conventional apparatus.

Second Embodiment

Figure 5:
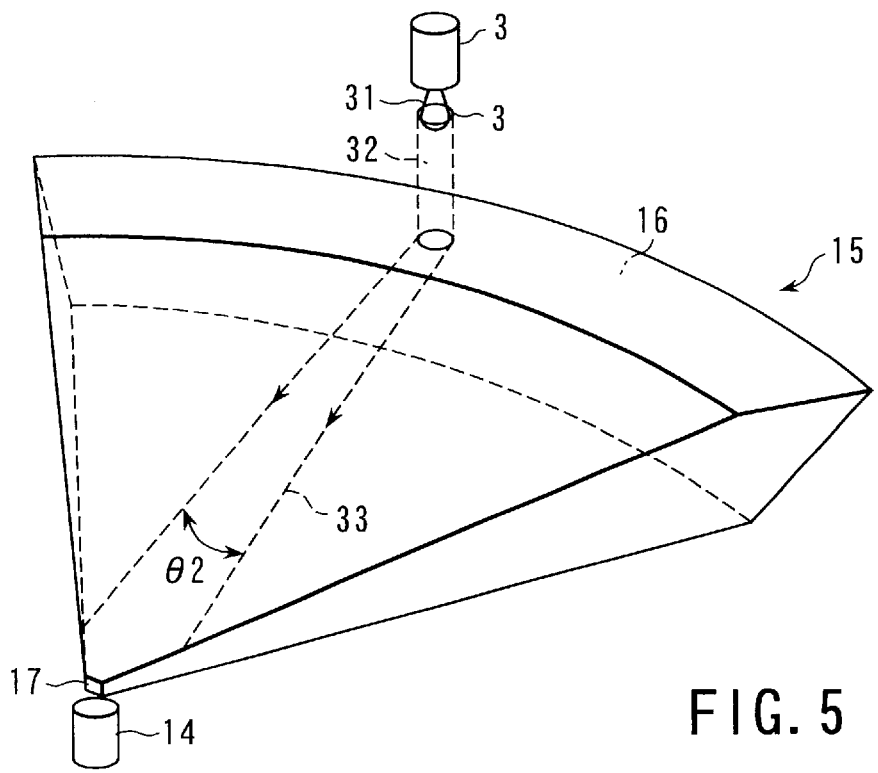
FIG. 5 is an oblique view schematically showing the construction of an optical guide member incorporated in a light transmitting apparatus between a rotor and a stator according to a second embodiment of the present invention.

FIG. 5 shows an apparatus for the light transmission between a rotor and a stator according to a second embodiment of the present invention.

The second embodiment differs from the first embodiment in that a lens 31 is arranged on the light-emitting side of the light-emitting element 13 so as to suppress the expansion of the light emission. In this case, a light beam 32 emitted from the lens 31 forms a substantially parallel light flux, making it possible to suppress the expansion of a light beam 33 reflected from the first reflecting surface 16 of the optical guide member 15. As a result, the light power received by the photo-detecting element 14 can be further increased.

It should also be noted that, in the second embodiment of the present invention, the light power received by the photo-detecting element 14 is set substantially constant even if a large distance is set between the light-emitting element 13 and the optical guide member 15. To be more specific, it is possible to increase the distance between the rotor 11 and the stator 12 described previously so as to increase the width of the design. Also, if the photo-detecting element 14 and the optical guide member 15 are made integral so as to form a light receiver, the first reflecting surface 16 acts as a light collector. It follows that it is possible to use the light collector as a receiving apparatus of a LAN (Local Area Network).

As described above, according to the second embodiment of the present invention, it is possible to further increase the light power received by the photo-detecting element 14. It is also possible to ensure a broader tolerance between the rotor 11 and the stator 12.

Third Embodiment

Figure 6:
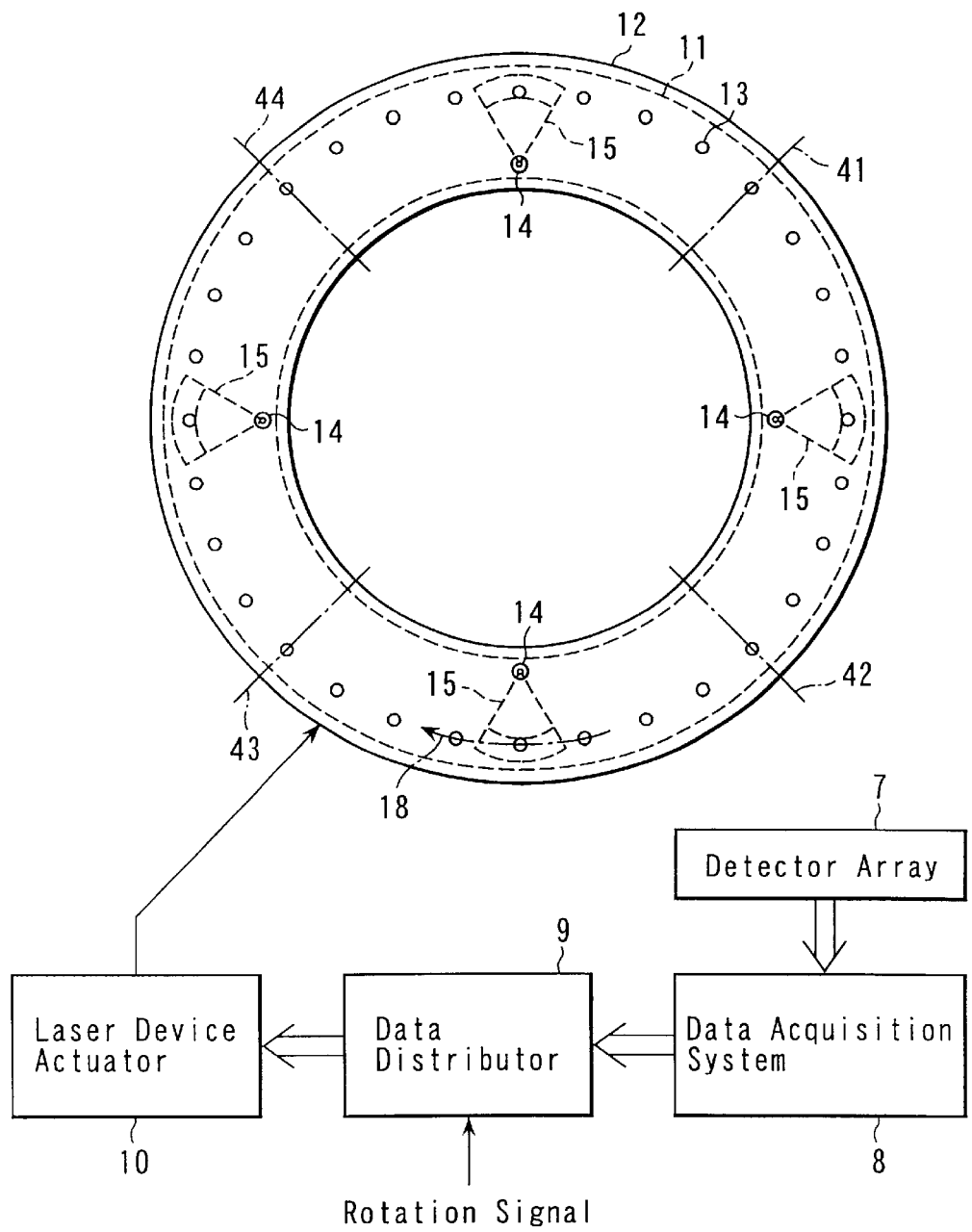
FIG. 6 is a front view schematically showing an apparatus for the light transmission between a rotor and a stator according to a third embodiment of the present invention.

FIG. 6 shows the construction of the light transmission apparatus between a rotor and a stator according to a third embodiment of the present invention.

In the third embodiment of the present invention, a plurality of light-emitting elements 13, i.e., 32 light-emitting elements in this embodiment, are divided into a plurality of groups, i.e., four groups in this embodiments, in the rotating direction of the rotor 11 along dividing lines 41 to 44 that are apart from each other by 45°. The light-emitting elements 13 of the same group are driven to emit a light beam according to the same data. On the other hand, a plurality of photo-detecting elements 14 are equidistantly arranged on the stator 12 in the rotating direction of the rotor 11. The number of photo-detecting elements 14 is equal to the number of groups of the light-emitting elements 13. In this embodiment, four photo-detecting elements 14 are mounted to the stator 12. Further, the optical guide member 15 is also mounted to the stator 12 in a manner to conform with the photo-detecting element 14. In other words, four optical guide members 15 are mounted to the stator 12 in this embodiment.

Different data are allotted to the four groups of the light-emitting elements 13 divided by the dividing lines 41 to 44. To be more specific, every time the light-emitting element 13 is moved to reach the dividing lines 41 to 44 in accordance with rotation of the rotor 11, the data are distributed by a data distributor 9, and the light-emitting elements 13 of the same group are driven by driving signals of the same phase and the same polarity on the basis of the distributed data so as to emit light beams. It follows that, by equidistantly arranging a set of the photo-detecting element 14 and the optical guide member 15, it is possible to achieve the light beam transmission of the four different data. To be more specific, the signal generated from the X-ray detection array 7 is supplied to the data acquisition system 8 so as to be converted into a digital signal and stored in the data acquisition system 8. The digital data collected in the data acquisition system 8 is supplied to the data distributor 9 mounted to the rotor 1. A rotation signal generated from a rotation detector (not shown) for detecting the rotation of the rotor 1 is supplied to the data distributor 9, and the digital data is separated in accordance with the rotating position of the rotor 1 so as to be supplied to the laser device actuator 10. A driving signal is supplied from the laser device actuator 10 to the light-emitting element in each group in accordance with the digital data, and the light beam emitted from the light-emitting element in each group is transmitted to the photo-detecting element mounted to the stator 2. As a result, the light beam modulated in accordance with the digital data is transmitted from the light-emitting element to the photo-detecting element.

As described above, according to the third embodiment of the present invention, it is possible to realize a light transmission apparatus between a rotor and a stator which permits the light transmission by multiplexing the data. It follows that the light transmission apparatus according to the third embodiment of the present invention is adapted for use in, for example, a multi-slice type X-ray CT apparatus which permits obtaining a large number of tomographic images simultaneously.

Fourth Embodiment

Figure 7:
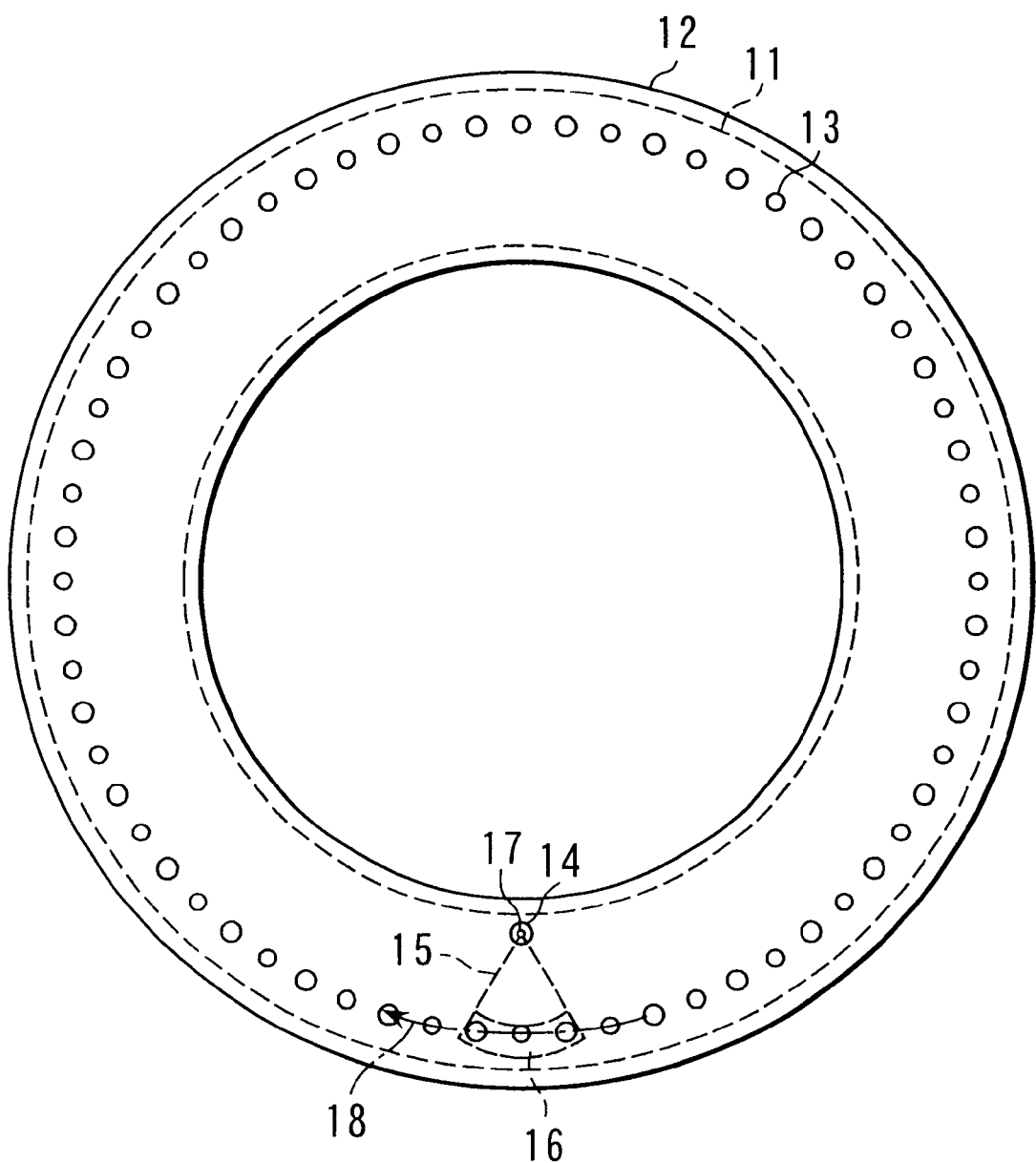
FIG. 7 is a front view schematically showing an apparatus for the light transmission between a rotor and a stator according to a fourth embodiment of the present invention.

FIG. 7 shows the construction of a light transmitting apparatus between a rotor and a stator according to a fourth embodiment of the present invention.

The light transmitting apparatus between a rotor and a stator according to the fourth embodiment of the present invention, which is equal in its basic construction to the apparatus according to the first embodiment of the present invention, differs from the first embodiment in that the number of light-emitting elements 13 equidistantly arranged in the rotating direction of the rotor 11 is increased in the fourth embodiment so as to permit at least two light-emitting elements 13 to be kept positioned within the arcuate portion of the optical guide member 15. To be more specific, 64 light-emitting elements 13 are arranged in the fourth embodiment so as to permit two light-emitting elements 13 to be kept positioned within the arcuate portion of the optical guide member 15.

In other words, the arc of the arcuate portion of the optical guide member 15 is made longer than the distance between the adjacent light-emitting elements 13 in the fourth embodiment of the present invention so as to permit the light beams emitted from at least two light-emitting elements 13 to be incident on the photo-detecting element 14 via the optical guide member 15.

Among the constituents of the light transmitting apparatus between a rotor and a stator, the LD constituting the light-emitting element 13 is one of the parts having the lowest reliability. Therefore, in the fourth embodiment of the present invention, in which the light beams emitted from at least two light-emitting elements 13 are allowed to be incident on the photo-detecting element 14, it is possible to perform the data transmission even if one of the light-emitting elements consisting of laser diodes (LD) goes wrong, so as to markedly improve the reliability of the apparatus.

Fifth Embodiment

Figures 8A, 8B:
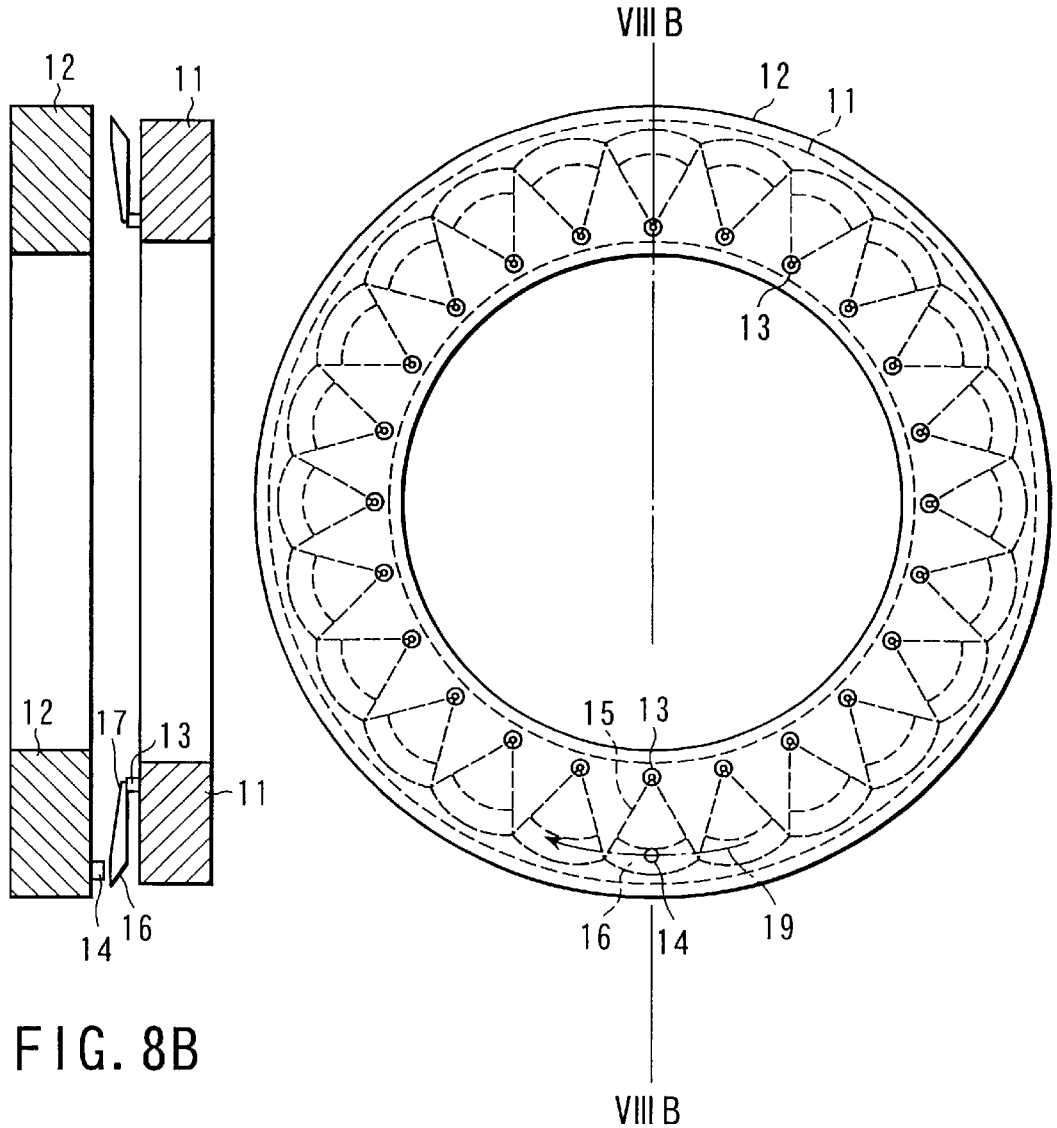
FIG. 8A is a front view schematically showing an apparatus for the light transmission between a rotor and a stator according to a fifth embodiment of the present invention.
FIG. 8B is a cross sectional view along the line VIIIB–VIIIB' shown in FIG. 8A.

FIGS. 8A and 8B collectively show the construction of a light transmitting apparatus between a rotor and a stator according to a fifth embodiment of the present invention.

The fifth embodiment differs from any of the embodiments described previously in that the optical guide member 154 is fixed to the rotor 11. To be more specific, in the fifth embodiment of the present invention, the optical guide member 15 is positioned and fixed such that the second reflecting surface 17 of the optical guide member 15 is positioned on the side of the light-emitting element 13 of the rotor 11.

Figure 9:
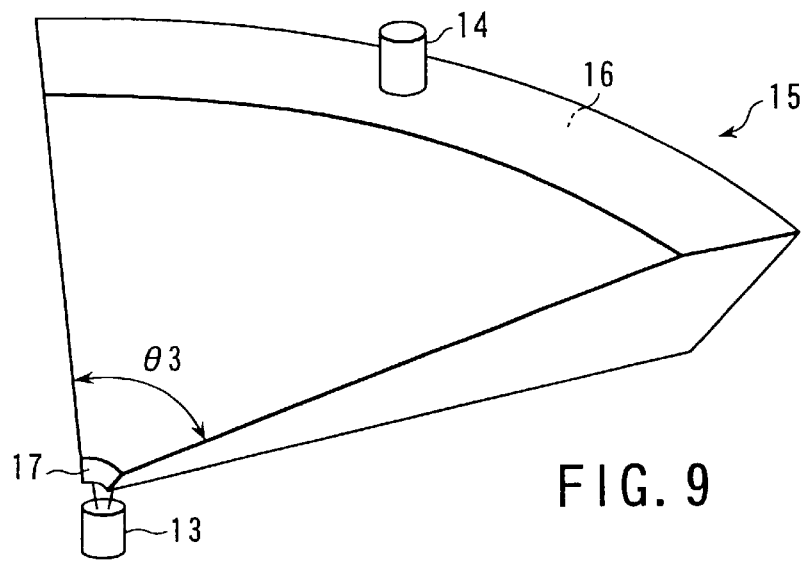
FIG. 9 is an oblique view showing the construction of the optical guide member shown in FIGS. 8A and 8B.

It should also be noted that 24 light-emitting elements 13, which is smaller by 8 than that in the first embodiment, are arranged on a circumferential region on the position closer to the inner circumferential surface of the rotor 1. On the other hand, only one photo-detecting element 14 is arranged on a position closer to the outer circumferential surface of the stator 12. The optical guide member 15 is fan-shaped as shown in FIG. 9, as in any of the embodiments described previously. In the fifth embodiment, however, the edge of the first reflecting surface 16 is partly cut away so as to make continuous the first reflecting surface 16 formed in the arcuate portion. The first reflecting surface 16 of the optical guide member 15 is moved over the photo-detecting element 14 along a moving path 19.

As described previously, the light beam emitted from the light-emitting element 13 is diverged in general. Therefore, the second reflecting surface 17 is imparted with a greater curvature in order to permit the light beam emitted from the light-emitting element 13 to be radiated over the entire region. By controlling the expansion of the light beam emitted from the light-emitting element 13 and the curvature of the second reflecting surface 17, the light beam is allowed to reach the entire region of the first reflecting surface 16. Therefore, since the light power received by the photo-detecting element 14 is decreased with increase in the area of the first reflecting surface 16, it is necessary to design the apparatus in view of the light power budget.

In the fifth embodiment of the present invention, the number of optical guide members 15 is equal to the number of light-emitting elements 13. However, if the optical guide member is manufactured by employing a molding process using an acrylic resin, it is possible to manufacture the optical guide member 15 with a low manufacturing cost. Also, the fifth embodiment differs from any of the embodiments described previously in that it is possible to further decrease the light-emitting elements 13 and the driving IC's. It follows that it is possible to decrease the manufacturing cost of the entire apparatus.

As described above, according to the fifth embodiment of the present invention, it is possible to further decrease the number of light-emitting elements 13 and the number of driving IC's, making it possible to realize a light transmitting apparatus between a rotor and a stator, which permits further decreasing the manufacturing cost.

Sixth Embodiment

In the first embodiment of the present invention described previously, the optical guide member 15 is formed of a transparent acrylic resin. However, it is also possible to use another material for manufacturing the optical guide member 15. For example, where the optical guide member 15 is formed of glass, the optical guide member 15 is not deformed even if the rotor 11 and the stator 12 are put under an environment of a high temperature so as to achieve a stable data transmission. On the other hand, a light transmitting apparatus of a lightweight can be achieved by using a relatively light material such as polycarbonate for manufacturing the optical guide member 15.

As described above, it is possible to provide a light transmitting apparatus between a rotor and a stator conforming with the special conditions of use by changing appropriately the material of the optical guide member 15.

Seventh Embodiment

In the embodiments described previously, the optical guide member 15 is formed of a transparent material such as an acrylic resin, glass or polycarbonate. However, it is also possible to apply a suitable coating of a metal film or a white film to the surface of the transparent base material. By applying the coating, it is possible to prevent the light loss caused by the attachment of dust to the optical guide member 15. Needless to say, such a coating should not be applied to some portions of the surface of the optical guide member 15 including at least the incident portion of the light beam on the light-emitting element 13 and the emitting portion where the light beam is emitted toward the photo-detecting element 14.

The coating material applied to the surface of the optical guide member 15 includes, for example, at least one metal material selected from the group consisting of Au, Al, Pt, Ag, Fe, Ni, Cu, Sn, Pb, Ti, Co, Mo, Zn and Cr, an alloy of these metal materials, a white acrylic resin, and a white resin material having a relatively high reflectivity such as a fluorine-containing resin.

Figure 10:
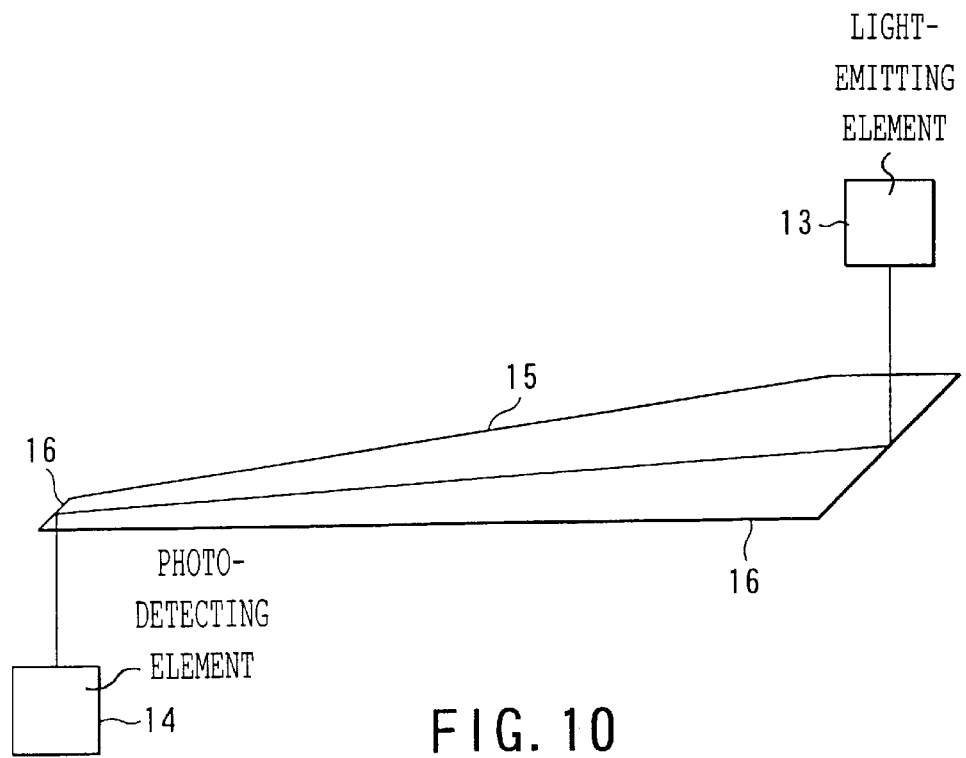
FIG. 10 is a cross sectional view showing the construction of the optical guide member incorporated in a light transmitting apparatus according to still another embodiment of the present invention.

The present invention can be worked in variously modified fashions. For example, in the embodiments described above, the optical guide member 15 has a pentagonal cross sectional shape including the first reflecting surface 16 and the second reflecting surface 17. However, it is possible for the optical guide member 15 to have a rectangular cross sectional shape as shown in FIG. 10. It is also possible to use an optical fiber as the optical guide member. Further, the technical idea of the present invention can be applied to a light transmission apparatus between a rotor and a stator, in which the light-emitting element is arranged on the side of the stator with the photo-detecting element arranged on the side of the rotor. Still further, the constructions in the various embodiments of the present invention described above can be combined appropriately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for transmitting a light beam modulated in accordance with data to be transmitted between a rotor and a stator, the rotor and the stator facing each other with a gap therebetween, and the rotor being rotated along a rotor plane, the apparatus comprising:

a plurality of light-emitting elements configured to emit light beams in accordance with the data to be transmitted, the light-emitting elements being mounted on the rotor and arranged on a first reference circle on the rotor plane;

a photo-detecting element configured to sequentially detect the light beams emitted from the plurality of light-emitting elements, the photo-detecting element being mounted on the stator and arranged on a second reference circle different from the first reference circle and coaxial with the first reference circle so as to face the rotor plane; and an optical guide member configured to guide at least one of the light beams emitted from the light-emitting elements to the photo-detecting element, the optical guide member being arranged in the gap between the stator and the rotor, made of a transparent material, and fixed to one of the stator and the rotor.

2. The light transmitting apparatus according to claim 1, wherein the optical guide member has a substantially fan-shaped form and includes a substantially arcuate surface portion and a proximal end portion, the arcuate surface portion being located on the first reference circle to receive the light beam from the light-emitting element and the proximal end portion being located on the second reference circle to direct the light beam to the photo-detecting element, the optical guide member further includes a first reflecting surface arranged at a predetermined angle to the optical axis of the light-emitting element to reflect the light beam passing through the arcuate surface portion, and a second reflecting surface arranged substantially in parallel to the first reflecting surface to reflect the light beam from the first reflecting surface to the proximal end portion.

3. The light transmitting apparatus according to claim 1, wherein the optical guide member has a substantially fan-shaped form and includes a substantially arcuate surface portion and a proximal end portion, the arcuate surface portion being located on the second reference circle to receive the light beam from the light-emitting element and the proximal end portion being located on the first reference circle to direct the light beam to the photo-detecting element, the optical guide member further includes a first reflecting surface arranged at a predetermined angle to the optical axis of the light-emitting element to reflect the light beam passing through the arcuate surface portion, and a second reflecting surface arranged substantially in parallel to the first reflecting surface to reflect the light beam from the first reflecting surface to the proximal end portion.

4. The light transmitting apparatus according to claim 1, further comprising a lens configured to convert the light beam emitted from the light-emitting element into a substantially collimated light beam and guide the light beam to the optical guide member.

5. The light transmitting apparatus according to claim 2, further comprising a lens configured to convert the light beam emitted from the light-emitting element into a substantially collimated light beam and to guide the light beam to the optical guide member.

6. The light transmitting apparatus according to claim 3, further comprising a lens configured to convert the light beam emitted from the light-emitting element into a substantially collimated light beam and to guide the light beam to the optical guide member.

7. The light transmitting apparatus according to claim 1, wherein the optical guide member has a light incident surface located on one of the first and second reference circles to receive the light beam from the light-emitting element, a light projection surface portion located on another one of the first and second reference circles to direct the light beam to the photo-detecting element, and other surfaces coated with a light shielding film.

8. The light transmitting apparatus according to claim 7, wherein the light shielding film is one of a white film layer and a metal film layer.

9. An apparatus for transmitting a light beam modulated in accordance with data to be transmitted between a rotor and a stator, the rotor and the stator facing each other with a gap therebetween, and the rotor being rotated along a rotor plane, the apparatus comprising:
a plurality of groups of light-emitting elements, each group configured to emit light beams in accordance with the same data to be transmitted, the light-emitting elements being mounted on the rotor and arranged at predetermined intervals on a first reference circle on the rotor plane;
a plurality of photo-detecting elements corresponding to the groups of the light-emitting elements, respectively, and each configured to sequentially detect the light beams emitted from each of the groups of the light-emitting elements, the photo-detecting elements being substantially equidistantly mounted on the stator and arranged on a second reference circle different from the first reference circle and coaxial with the first reference circle so as to face the rotor plane; and
optical guide members each configured to guide at least one of the light beams emitted from a corresponding group of the light-emitting elements to the corresponding photo-detecting element, the optical guide members being arranged in the gap between the stator and the rotor, made of a transparent material, and fixed to one of the stator and the rotor.

10. The light transmitting apparatus according to claim 9, wherein each of the optical guide members has a substantially fan-shaped form and includes a substantially arcuate surface portion and a proximal end portion, the arcuate surface portion being located on the first reference circle to receive the light beam from the light-emitting element and the proximal end portion being located on the second reference circle to direct the light beam to the photo-detecting element, the optical guide member further includes a first reflecting surface arranged at a predetermined angle to the optical axis of the light-emitting element to reflect the light beam passing through the arcuate surface portion, and a second reflecting surface arranged substantially in parallel to the first reflecting surface to reflect the light beam from the first reflecting surface to the proximal end portion.

11. The light transmitting apparatus according to claim 9, wherein each of the optical guide members has substantially fan-shaped form and includes a substantially arcuate surface portion and a proximal end portion, the arcuate surface portion being located on the second reference circle to receive the light beam from the light-emitting element and the proximal end portion being located on the first reference circle to direct the light beam to the photo-detecting element, the optical guide member further includes a first reflecting surface arranged at a predetermined angle to the optical axis of the light-emitting element to reflect the light beam passing through the arcuate surface portion, and a second reflecting surface arranged substantially in parallel to the first reflecting surface to reflect the light beam from the first reflecting surface to the proximal end portion.

12. The light transmitting apparatus according to claim 10, wherein each group corresponds to a plurality of the light-emitting elements which are so arranged that the two light beams emitted from two of the light-emitting elements simultaneously enter the arcuate portion of the optical guide member.

13. The light transmitting apparatus according to claim 11, wherein each of the group corresponds to the two light-emitting elements which are so arranged that the two light beams emitted from the two light-emitting elements are simultaneously enter into the arcuate portion of the optical guide member.

14. The light transmitting apparatus according to claim 9, wherein each of the optical guide member has a light incident surface located on one of the first and second reference circles to receive the light beam from the light-emitting element, the light projection surface portion being located on another one of the first and second reference circles to direct the light beam to the photo-detecting element, and other surfaces being coated with a light shielding film.

15. The light transmitting apparatus according to claim 14, wherein the light shielding film is one of a white film layer and a metal film layer.

16. An X-ray CT apparatus, comprising:
an X-ray tube configured to emit X-rays;
a rotor configured to support the X-ray tube, the rotor being rotated along a rotor plane on which a first reference circle is defined;
a stator configured to rotatably support the rotor, a second reference circle different from the first reference circle being defined on the stator, the first and second circles being coaxially arranged and the stator facing the rotor with a gap therebetween;

a driving mechanism configure to rotate the rotor with the X-ray tube;

a plurality of light-emitting elements configured to emit light beams in accordance with the data to be transmitted, the light-emitting elements being mounted on the rotor and arranged on the first reference circle on the rotor plane;

a photo-detecting element configured to detect the light beams emitted from the plurality of light-emitting elements the photo-detecting element being mounted on the stator and arranged on the second reference circle so as to face the rotor plane; and an optical guide member configured to guide at least one of the light beams emitted from the light-emitting element to the photo-detecting element, the optical guide member being arranged in the gap between the stator and the rotor, made of a transparent material, and fixed to one of the stator and the rotor.

17. The X-ray CT apparatus according to claim 16, wherein the optical guide member has a substantially fan-shaped form and includes a substantially arcuate surface portion and a proximal end portion, the arcuate surface portion being located on the first reference circle to receive the light beam from the light-emitting element and the proximal end portion being located on the second reference circle to direct the light beam to the photo-detecting element, the optical guide member further includes a first reflecting surface arranged at a predetermined angle to the optical axis of the light-emitting element to reflect the light beam passing through the arcuate surface portion, and a second reflecting surface arranged substantially in parallel to the first reflecting surface to reflect the light beam from the first reflecting surface to the proximal end portion.

18. The X-ray CT apparatus according to claim 16, wherein the optical guide member has a substantially fan-shaped form and includes a substantially arcuate surface portion and a proximal end portion, the arcuate surface portion being located on the second reference circle to receive the light beam from the light-emitting element and the proximal end portion being located on the first reference circle to direct the light beam to the photo-detecting element, the optical guide member further includes a first reflecting surface arranged at a predetermined angle to the optical axis of the light-emitting element to reflect the light beam passing through the arcuate surface portion, and a second reflecting surface arranged substantially in parallel to the first reflecting surface to reflect the light beam from the first reflecting surface to the proximal end portion.

19. The X-ray CT apparatus according to claim 16, further comprising a lens configured to convert the light beam emitted from the light-emitting element into a substantially collimated light beam and guide the light beam to the optical guide member.

20. The X-ray CT apparatus according to claim 16, wherein the optical guide member includes a light incident surface located on one of the first and second reference circles to receive the light beam from the light-emitting element, the light projection surface portion located on another one of the first and second reference circles to direct the light beam to the photo-detecting element, and other surfaces coated with a light shielding film.

* * * * *